United States Patent [19]
Georgiou et al.

[11] Patent Number: 5,264,365
[45] Date of Patent: Nov. 23, 1993

[54] PROTEASE-DEFICIENT BACTERIAL STRAINS FOR PRODUCTION OF PROTEOLYTICALLY SENSITIVE POLYPEPTIDES

[75] Inventors: George Georgiou, Austin, Tex.; Francois Baneyx, Thenon, France

[73] Assignee: Board of Regents, The University of Texas System, Austin, Tex.

[21] Appl. No.: 612,696

[22] Filed: Nov. 9, 1990

[51] Int. Cl.$^5$ .................. C12N 1/20; C12N 15/01; C12P 21/00
[52] U.S. Cl. .................. 435/252.8; 435/69.1; 435/172.3
[58] Field of Search .................. 435/69.1, 71.2, 172.3, 435/252.3

[56] References Cited

U.S. PATENT DOCUMENTS

| | | | |
|---|---|---|---|
| 4,656,131 | 4/1987 | Kiyano et al. | 435/69.1 |
| 4,948,729 | 8/1990 | Piatak, Jr. et al. | 436/68 |

FOREIGN PATENT DOCUMENTS

WO88/05821 8/1988 PCT Int'l Appl.
WO89/02465 3/1989 PCT Int'l Appl.

OTHER PUBLICATIONS

Dykstra et al., *J. of Bacteriol.*, 163(3) 1055–1059 (1985).
Grodberg et al., *J. of Bacteriol.*, 170(3) 1245–1253 (1988).
Baneyx et al. *J. Bacteriol.* 173(8): 2696–2703 (1991).
Maniatis et al., In Molecular Cloning: A Laboratory Manual, Cold Spring Harbor, N.Y., Cold Spring Harbor Lab. Press (1982).
Ausubel et al., in *Current Protocols in Molecular Biol.*, John Wiley & sons, New York, N.Y. (1987).
Baneyx, F. and Georgiou, G., *Journal of Bacteriology*, 172(1): 491–494 (Jan. 1990).
Swany, K. H. S. and Goldberg, A. L., "Subcellular Distribution of Various Proteases in *Eschercia coli*", *J. of Bacter.*, 149(3): 1027–1033 (Mar. 1982).
Strauch, K. L. and Beckwith, J., *Proc. Natl. Acad. Sci. USA*, 85:1576–1580 (Mar. 1988).
Cheng, et al., *Journal of Bacteriology*, 140(1):125–130 (Oct. 1979).
Elish, et al., "Biochemical Analysis of Spontaneous fepA Mutants of *Escherchia coli*", *J. Gen. Microbiology*, 134:1355–1364 (1988).
McIntosh, et al., *Journal of Bacteriology*, 137(1):653–657 (Jan. 1979).
Chaudhury, A. M. and Smith, G. R., "*Escherchia coli* recBC Deletion Mutants", *J. of Bacteriology*, 160(2):788–791 (Nov. 1984).
Russell, et al., *Journal of Bacteriology*, 171(5):2609–2613 (May 1989).
Dykstra, et al., *Journal of Bacteriology*, 157(1):21–27 (Jan. 1984).
Pacaud, Mcihéle, *The Journal of Biological Chemistry*, 257(8):4333–4339 (Apr. 1982).
Palmer, S. M. and St. John, A. C., *Journal of Bacteriology*, 169(4):1474–1479 (Apr. 1987).
Strauch, et al., *Journal of Bacteriology*, 171(5):2689–2696 (May 1989).
Lazdunski, A. M., "Peptides and proteases of *Escherchia coli* and *Salmonella typhimurium*", *FEMS Microbiology Reviews*, 63:265–276 (1989).
Baneyx, F. and Georgiou, G., *Enzyme Microb. Technol.*, 11:559–567 (Sep. 1989).
Georgiou, et al., *Biotechnology and Bioengineering*, 32:741–748 (1988).

(List continued on next page.)

*Primary Examiner*—Richard A. Schwartz
*Assistant Examiner*—Nancy T. Vogel
*Attorney, Agent, or Firm*—Arnold, White & Durkee

[57] ABSTRACT

The invention relates to the construction of protease-deficient *Escherichia coli* hosts which when combined with an expression system are useful for the production of proteolytically sensitive polypeptides. The invention also includes examples of particular mutant *Escherichia coli* deficient in up to four proteases.

6 Claims, 8 Drawing Sheets

OTHER PUBLICATIONS

Herschko, Avram and Ciechanover, Aaron, "Mechanisms of Intracelular Protein Breakdown", *Ann. Rev. Biochem.*, 51:335-364 (1982).

Huse, et al., *Science*, 246:1275-1281 (Dec. 1989).

Goldberg, A. L. and St. John, A. C., *Ann. Rev. Biochem.*, 45:747-803 (1976).

Weichenhan, D. and Wachkernagel, W., *Molecular Microbiology*, 3(12):1777-1784 (1989).

Georgiou, G., "Optimizing the Production of Recombinant Proteins in Microorganisms", *AIChE Journal*, 34(8):1233-1248 (Aug. 1988).

Smith, et al., *The Journal of Biological Chemistry*, 246(10):3320-3329 (May 1971).

Nossal, N. G. and Heppel, L. A., *The Journal of Biological Chemistry*, 241(13):3055-3062 (Jul. 1966).

Laemmli, U. K., *Nature* (London), 227:680-685 (1970).

Chang, A. C. and Cohen, S. N., *Journal of Bacteriology*, 134(3):1141-1156 (Jun. 1978).

Miller, C. G. in *Escherichia coli* and *Salmonella typhimurium:* Cellular and Molecular Biology, vol. 1, F. C. Neidhardt, Ed., American Society for Microbiology, Washington, D.C., 680-691 (1987).

PROTEASE-DEFICIENT BACTERIAL STRAINS FOR PRODUCTION OF PROTEOLYTICALLY SENSITIVE POLYPEPTIDES

The United States Government may have certain rights in the present invention pursuant to the terms of Grant No. CBT-8657471 awarded by the National Science Foundation.

BACKGROUND OF THE INVENTION

1. Field of the Invention

The invention relates to the construction of protease-deficient bacteria, particularly *E. coli*, using methods of recombinant DNA technology, and to the expression of polypeptides by the protease-deficient cells. In a particular aspect of the invention, improved yields of protease sensitive polypeptide products are accumulated when a multiply protease-deficient *E. coli* is used to generate proteolytically sensitive proteins.

2. Description of Related Art

*Escherichia coli* has been the most widely used microorganism for the production of commercially important recombinant proteins. Despite the lack of certain kinds of post-translational processing and the production of endotoxins, *E. coli* presents numerous advantages for protein expression. Its genetics are well understood, it can be grown to high densities on inexpensive substrates, and fermentation scale-up is straightforward (1).

A number of useful eukaryotic proteins have been cloned and expressed in *E. coli* including human insulin and proinsulin, human and bovine somatotropins, interferons and tissue plasminogen activator. Recently, Huse and coworkers (2) constructed a bacteriophage lambda system which allows the expression and rapid screening of mouse $F_{ab}$ antibody fragments in *E. coli*. For most biotechnology applications it is advantageous to secrete the protein from the cytoplasm. Secretion of the polypeptide product can facilitate correct folding, reduce protein degradation and simplify subsequent purification steps.

One of the major problems associated with the expression of heterologous polypeptides in *Escherichia coli* is the degradation of cloned gene products by host-specific proteases (3). It has been shown that, as in eukaryotic cells, energy-dependent processes are important for the degradation of *E. coli* proteins with abnormal conformations (4,5). However, most *E. coli* proteases hydrolyze peptide bonds via an energy-independent pathway. At least 25 proteases and peptidases have been identified in different cellular compartments of *E. coli* (6,7). The biochemical characterization of these enzymes is incomplete and there is relatively little information on their physiological role. One or more of these proteases may act upon any given polypeptide to effect degradation and thereby reduce yields, sometimes quite drastically.

One approach to solving the problem of low polypeptide production in bacterial host cells has been the use of an inducible expression system in combination with a constitutively protease-deficient bacterial host strain. This method will operate to increase polypeptide yields only if the deficient protease has as its substrate the target polypeptide which is being expressed. For example, the production of an immunologically functional antibody fragment in a constitutively lon$^-$ and/or htpR$^-$ *E. coli* strain produced low yields (8) even though such strains have been shown to have a general defect in protein degradation.

Several strains of *E. coli* deficient in proteases or genes controlling the regulation of proteases are known (9-11). Some of these strains have been used in attempts to efficiently produce proteolytically sensitive polypeptides, particularly those of potential medical or other commercial interest.

Some singly protease-deficient mutants of *Escherichia coli* have been prepared. These include a degP deficient genetically engineered strain and a spontaneous mutant, UT4400, in which the entire ompT gene together with a sizable piece of adjacent DNA have been deleted from the chromosome (12). Mutants carrying large deletions in the Protease III (ptr) gene including adjacent genes recC, recB and recD, have been isolated (10). However, since the adjacent genes are important for cell viability and stable propagation of plasmids in *Escherichia coli*, the mutant strains exhibit growth defects and low protein production. A Protease III mutant strain has also been isolated after chemical mutagenesis (13).

Using a similar rationale, but a genetic engineering approach, a method of mutagenizing *Escherichia coli* to produce a cell with a defective periplasmic protease has been described (9). A degP deletion mutant was constructed and recombined into an *E. coli* chromosome (14). Some workers have shown that the proteolytically sensitive fusion protein, protein A-$\beta$-lactamase, is stabilized three-fold in such a deg mutant (15,16).

Most proteins are degraded by more than one protease. Therefore, the use of mutants deficient in the synthesis of a single enzyme can only partially prevent the degradation of the product. Inactivation of multiple proteolytic enzymes may lead to higher production. The challenge is complex, however, because there is no assurance that disablement or deletion of any given protease or combination of proteases will result in a viable or unchanged host cell or that such manipulation will avoid the precipitation of toxic events within the cell.

The genetically engineered protease-deficient microorganisms of the present invention have shown unexpectedly improved yields of proteolytically sensitive polypeptide products while maintaining good growth and cell viability. For the first time, a microorganism deficient in Protease III has been engineered which, unlike mutants previously isolated, is not defective in the gene product of adjacent genes recC, recB or recD. In addition, three doubly protease defective microorganisms and a triply defective microorganism have been engineered. The use of these microorganisms grown under optimized conditions significantly broadens the potential to produce commercially valuable polypeptides.

SUMMARY OF THE INVENTION

The present invention relates generally to mutant protease-deficient gram-negative bacteria, preferably *Escherichia coli*, that are capable of significantly enhancing production of proteolytically sensitive polypeptides when transformed with appropriate expression vectors. In particular, multiply protease-deficient bacterial strains have been constructed. These strains are viable and show good growth characteristics. They are useful in processes for the production of a wide range of proteolytically sensitive polypeptides of commercial interest.

In general, mutant organisms are constructed from strains of unicellular organisms, preferably gram-negative organisms, for example *Salmonella typhimuriu, Erwina carotavora* and *Klebsiella pneumoniae*. Most preferable is *Escherichia coli*. These strains will preferably be capable of encoding at least two secreted proteases from at least two genes. The mutants constructed from these strains will be suitable hosts for transformation with a variety of expression vectors resulting in the production of various proteins. The proteins produced are not native to the mutant host; that is, these proteins are heterologous. The mutants are characterized in that many of the proteins that can be produced by virtue of the expression systems present in the cell will not be degraded because of deficiencies in at least two of the genes that normally produce proteolytic enzymes.

In a particular aspect of the invention the mutant organism has a deficiency in proteases OmpT, DegP and Protease III. Deficiency in each of these proteases is caused by a mutation in the respective genes coding for these proteases. These genes are omPT, degP and ptr. The mutations may be deletions or engineered mutations such as a cut in the gene may be produced and the gene subsequently reinserted into the bacterial genome. In one embodiment of the present invention the triply protease-deficient mutant microorganism was constructed by transferring a ptr mutation from a mutated strain into another mutant organism having ompT and degP deletions. As an example meant only to illustrate and not to limit, ompT and/or degP deletion mutants may be selected by standard procedures. For example, mutant strain UT4400 is a spontaneous mutant in which the entire ompT gene together with a sizable piece of adjacent DNA has been deleted from the chromosome. P1 transduction may be used to transfer chromosomal DNA from an ompT mutant into a degP mutant such as KS474. A triply protease-deficient mutant strain may then be constructed by generalized P1 transduction transfer of the ptr gene mutation from an appropriate strain into double ompT degP mutants.

It is to be understood that ptr degP ompT mutants may also be constructed by transferring a ptr mutation into any genetic background deficient in DegP and OmpT proteolytic activities by using P1 transduction or similar techniques. Alternatively, such mutants may be constructed by transferring an ompT mutation into any genetic background deficient in Protease III and DegP or by transferring a degP mutation in any genetic background deficient in Protease III and OmpT by using P1 transduction or similar techniques. A particular embodiment of this mutant organism is the *E. coli* stain SF120 having ATCC Accession No. 55099 which was deposited on Oct. 10, 1990. The OmpT DegP and Protease III deficiencies characteristic of the mutant organisms that are triply protease-deficient may be characterized in different ways depending on the nature of the mutation in the respective genes which code for these proteases. For example, the mutations in the genes coding for these proteases may be due to deletions and such deletions result in no product of the proteins that exhibit the proteolytic activity ascribed to DegP, OmpT and Protease III. However, not all mutations are deletions and similar results can be obtained with other mutations including point, missense, nonsense and frameshift mutations, mutations resulting from ultraviolet or chemical or any general mutagenesis technique, or a combination thereof. In certain cases, mutations in portions of the genes encoding the proteases may be such that a gene product is expressed but there is a substantial loss or even lack of proteolytic activity. Mutations in any one or more of the three genes may also result in either lack of gene product or products having substantially lowered activity.

In another aspect of this invention a mutant organism derived from a stain of unicellular organism capable of encoding Protease III has been prepared. This mutant is characterized as expressing a polypeptide product of genes recB, recC and recD while at the same time exhibiting a deficiency in the ptr gene product Protease III. Proteolytically sensitive proteins that may be produced by this mutant organism are not degraded because of the deficiency in Protease III or if they are degraded it is to a very small extent. The polypeptide product expressed by genes recB, recC and recD exhibits exonuclease V activity. The expression of this activity appears to be important for the viability of the organism and the stable propagation of expression vectors. Other ptr mutants reported appear to contain mutations involving deletions of the ptr gene as well as genes recB, recC and recD and hence, lack exonuclease V activity (10). The result of this appears to be a mutant microorganism that has poor growth characteristics and exhibits genetic instability. In contrast, the engineered mutant constructed as part of this invention exhibits normal exonuclease V activity although it lacks Protease III activity.

The degP ompT mutant organism is deficient in proteases DegP and OmpT due to a partial deletion of gene degP and a total deletion of ompT. This is not to say that the same result could not be achieved with other mutations of either gene resulting in each protease either lacking significant activity or not produced by the gene. OmpT degP mutants can be prepared by transferring an ompT mutation into any genetic background containing a degP mutation using P1 transduction. Alternatively, ompT degP mutants may be obtained by introducing a degP mutation into any genetic background containing an ompT mutation by using P1 transduction or a similar technique. Any ompT ptr or degT ptr mutant may be prepared by standard methods of P1 transduction to transfer a ptr mutation into an appropriate strain, usually *E. coli* containing a degP or ompT mutation. Alternatively, ompT ptr (or degP ptr) mutants can be constructed by transferring an ompT (or degP) mutation into any genetic background deficient in Protease III using P1 transduction. When these mutant strains are transformed with an appropriate expression vector, the proteolytically sensitive proteins expressed are recovered substantially intact, that is, with little or no degradation because of the deficiency in one or more proteases. Examples of strains which can be used have been deposited with ATCC with accession numbers 55099, 55100 and 55101.

An important aspect of the invention is a process for producing proteolytically sensitive proteins by using the mutant microorganisms described. The mutant organism selected is transformed with an expression vector capable of expressing at least one proteolytically sensitive polypeptide. It will be appreciated that there are numerous expression vectors which may be selected. For example, expression vector pFB3 is capable of expressing a protein A-$\beta$-lactamase fusion protein. Numerous other vectors are known which express other proteins or polypeptides, for example, proinsulin, phosphatase, immunoglobulin $F_v$ fragments, epidermal growth factor, interleukin, interferon, somatotropin and insulin-like growth factors. Different proteins will be more or less sensitive to different proteases normally produced by the microorganisms. Thus, depending on the nature and type of polypeptide expressed, the mutant organism selected for production of that polypeptide will contain particular protease deficiencies. The mutant organism containing the appropriate expression vector is then incubated in a suitable medium for a period of time allowing production of the desired protein and then the desired polypeptide product is recovered. In many instances it will be desireable to use a multiply protease-deficient mutant organism rather than a single protease-deficient microorganism.

The usefulness of protease-deficient strains for the expression of proteolytically sensitive polypeptides was tested on the fusion protein, protein A-β-lactamase. β-lactamase is a small monomeric protein involved in the hydrolysis of the β-lactam ring of many antibiotics such as penicillin, nitrocefin and cephaloridine while protein A binds with high affinity to the $F_c$ fragment of IgG antibodies. The fusion protein, expressed by the plasmid vector pFB3, is secreted into the periplasmic space of E. coli cells, where it assumes a fully bifunctional conformation, i.e., it displays IgG binding ability and penicillinase enzymatic activity comparable to those of the authentic protein A and β-lactamase, respectively. However, although both protein A and β-lactamase are stable under normal conditions when expressed in E. coli, the fusion protein is highly susceptible to proteolytic degradation. Most of the degradation occurs within the β-lactamase domain of the hybrid protein (15). Therefore, the amount of penicillinase activity (e.g., β-lactamase activity against benzylpenicillin) present in cells harboring the plasmid vector expressing the fusion protein is directly proportional to the amount of intact protein A-β-lactamase. This property makes protein A-β-lactamase a suitable substrate for developing methods to reduce proteolysis in E. coli. As way of example, the expression of the fusion protein, protein A-β-lactamase, is markedly enhanced when expressed from the doubly protease-deficient mutant degP ompT by comparison with expression either from ompT or degP deletion mutants. When the same expression vector is used to express the fusion protein from the triply deficient mutant microorganism deficient in genes degP, ompT and ptr the amount of fusion protein expressed is increased even further. This indicates that, in general, the greater the number of proteases lacking in the mutant organism, the more enhanced the yield of product recovery.

Expression of proteolytically sensitive polypeptides using the mutant microorganisms will be controlled to some extent by the medium in which they are grown and some of the components added to the medium. The mutant microorganisms described, all of which contain expression vectors, grow well in complex and in minimal media, for example, LB medium or M9 medium. Surprisingly, enhanced production of the proteins is observed when divalent zinc ions are added to the medium. A preferable concentration is between about 0.05 and 0.8 mM. Most preferable is a concentration of about 0.5 mM when complex media are utilized. The pH of the media is preferably maintained between 5.0 and 6.5. In degP ompT ptr mutants, expression of the protein A-β-lactamase fusion protein is most preferably obtained in complex medium containing 0.5 mM zinc ions at a pH of 5.5.

Although the mutant organisms described have been exemplified in singly, doubly and triply protease-deficient mutant organisms, it is clearly possible to create mutant organisms having deficiencies in more than three proteases. It is well known that many gram-negative bacteria express at least seven or eight different proteases that degrade secreted polypeptides. Thus, once the appropriate genes have been cloned and the gene products are known, it is possible to select deletions or other mutations for these singly protease-deficient organisms and, by standard means, to propagate such mutations in other strains which themselves already contain deletions or mutations in proteolytic activities. However, since viability and growth of the genetically constructed engineered organism may be of major concern, care must be taken to avoid the accidental deletion or mutagenesis of genes involved in cell viability, plasmid stability or other essential cellular processes and located in the vicinity of genes encoding proteolytic activities.

Those of skill in the art will recognize that the methods illustrated for the construction of doubly and triply protease-deficient mutant microorganisms are applicable to the construction of other multiply protease-deficient microorganisms. Generally, a mutant protease gene is isolated and then recombined into the chromosome. Subsequently the mutated gene is transferred into another mutant strain, for example one that is deficient in one or more different proteases. The multiply protease-deficient mutant thus generated is then employed for the inactivation of additional proteases by repeating this procedure. Several proteases other than Protease III, OmpT and DegP are known in E. coli, for example Protease I, Protease Mi, Protease V or Protease VI. Once the gene sequence for any protease is known, it may be cloned and amplified, subjected to mutagenesis and then used to transform other cells. The procedure may be repeated to produce higher multiplicities of protease deficiencies.

It is expected that the deactivation of a large number of proteolytic enzymes at some point will compromise the cell's viability. For this reason it is preferred that a set of strains deficient in different combinations of up to four proteases are generated. Strains containing defects in the subset of proteolytic enzymes that act on a particular protease sensitive polypeptide thus provide the highest possible production without compromising the cell's viability, protein synthetic capacity or genetic stability. Further, optimal growth conditions for each mutant will have to be determined as there may be some variations in medium, pH and trace element addition such as $Zn^{+2}$ supplementation.

DETAILED DESCRIPTION OF PREFERRED EMBODIMENTS

Materials and Methods

Strains, Plasmids, Bacteriophages and Media

The bacterial strains and plasmids used are listed in Table I. Bacteriophage T4 gene 2 mutant (N51am) was provided as a gift from E. Goldberg (Tufts Medical School, Dept. of Microbiology). Cultures were grown in LB medium (Difco) supplemented with 0.2% glucose and the appropriate concentrations of antibiotics. M9 medium was supplemented with 0.2% casein amino acid hydrolysate, 0.2% glucose and the appropriate antibiotics. W salts medium has been described (17) and consists of 10.5 g $K_2HPO_4$, 4.5 g $KH_2PO_4$, 0.102 g $MgSO_4.7H_2O$ per liter of solution containing 0.2% L-glutamine, 0.2% glucose, and 0.2% $(NH_4)_2SO_4$. Ampicillin, tetracycline, kanamycin and chloramphenicol were added to the growth medium as required at 50 μg/ml, 25 μg/ml, 50 μg/ml and 20 μg/ml final concentration respectively.

Mutant *E. coli* deficient in one or more genes encoding a protease have been deposited with the American Type Culture Collection (ATCC), 12301 Parklawn Drive, Rockville, Md. 20852 U.S.A. on Oct. 10. 1990. The bacteria are identified as *Escherichia coli* SF120 (ATCC 55099), *Escherchia coli* SG103 (ATCC 55100) and *Escherchia coli* SF110 (ATCC 55101) deficient respectively in ompT, degP and ptr genes (ATCC 55099), ptr gene (ATCC 55100), and ompT and degP genes (ATCC 55101).

TABLE I

| Strain or plasmid | Bacterial strains and plasmids. | | Source or reference |
|---|---|---|---|
| | | Genotype or characteristics | |
| Strain | | | |
| D301 | RP487 | recD1903 Δ(lacIZYA-u169) | 23 |
| JC7729 | K-12 | recB21 sbcB15 his327 leu(am) trpE9829 lac str321 thi | |
| KS272 | F⁻ | ΔlacX74 galE galK thi rpsL (strA) ΔPhoA(PvuII) | 14 |
| KS474 | KS272 | degP41(ΔPstI-Kanʳ) | 28 |
| SF100 | KS272 | ΔompT | 16 |
| SF101 | D301 | ptr32::ΩCatʳ | |
| SF103 | KS272 | ptr32::ΩCatʳ | |
| SF110 | KS272 | ΔompT degP41(ΔPstI-Kanʳ) | 16 |
| SF112 | KA272 | ΔompT ptr32::ΩCatʳ | |
| SF115 | KS272 | ptr32::ΩCatʳ degP41(ΔPstI-Kanʳ) | |
| SF120 | KS272 | ptr32::ΩCatʳ degP41(ΔPstI-Kanʳ) ΔompT | |
| Plasmid | | | |
| pACYC184 | 4.2 | kbp medium copy number plasmid; Catʳ Tetʳ | 29 |
| pCDK3 | pBR325 | derivative carrying a 19 kbp BamH I fragment mapping (thyA-argA). | 30 |
| pCS1 | pUC19 | derivative carrying a 3.2 kbp PvuI SpA-bla fragment from pFB3; Ampʳ. | 16 |
| pFB3 | 9.86 | kbp pBR322 derivative carrying SpA-bla; Ampʳ Kanʳ. | 15 |
| pFB5 | pCS1 | derivative carrying an 8 kbp Sal I fragment encoding ptr; Ampʳ. | |
| pFB6 | pFB5 | derivative (ptr32::ΩCat⁴); Ampʳ Catʳ. | |

Enzymes and Chemicals

Restriction and DNA modifying enzymes were purchased from Boehringer-Mannheim, New England Biolabs and Promega. All recombinant DNA procedures were performed according to Maniatis et al. (18) or Ausubel et al. (19). Oxidized insulin B-chain and penicillin G were obtained from Sigma. All chemicals used were of biological grade.

Southern Blots

Southern blots were performed essentially as described by Ausubel et al. (19). Genomic DNA was isolated as described (19), separated in 0.8% agarose gels and transferred overnight to nitrocellulose (Schleicher & Schuell BA85). DNA was crosslinked to nitrocellulose by baking for 2 hr at 80° C. in a vacuum oven. Nonradioactive digoxigenin-11-dUTP probes were prepared using the Genius system (Boehringer Mannheim) according to the manufacturer's instructions.

Pulse-Chase Experiments

Cells were grown in labeling medium supplemented with 19 amino acids but no methionine (20) to mid-exponential phase (OD=0.5 at 600 nm). 100 μCi of $^{35}$S-Met were added to the growth medium. After two to five minutes, 1 ml of 0.5 mg/ml cold methionine was added and a zero point taken immediately. At specified times after initiation of the chase, 1 ml samples were transferred to microfuge tubes kept on ice and containing 50 μl of 34 mg/ml chloramphenicol. The cells were centrifuged, washed with 1 ml of 10 mM Tris HCl, pH 8.0, resuspended in lysis buffer (10 mM Tris HCl, pH 8.0, 1% SDS, 1 mM EDTA) and boiled for 3 minutes. Immunoprecipitation was performed as described (16). Autoradiograms were scanned with a prototype digital Clayton video densitometer developed at the University of Texas by Larry Poulson.

Penicillinase and Insulin Degradation Assays 3 ml samples from cultures grown as specified were centrifuged at 8,000 ×g for 8 min, the pellets were resuspended in 3 ml 50 mM potassium phosphate, pH 6.5 and disrupted by French pressing at 20,000 psi. The insoluble fraction was removed by centrifugation. Penicillinase activities were measured by spectrophotometry at 240 nm as previously described (15) using a 0.5 g/l penicillin G solution in 50 mM potassium phosphate, pH 6.5 as a substrate.

For insulin assays, cells were grown overnight in LB medium supplemented with 0.2% glucose and the appropriate concentrations of antibiotics as required. Osmotic fractions were collected by the method of Nossal and Heppel (21) and concentrated using Amicon Centricon-10 microconcentrators. 30 μg of periplasmic proteins were mixed with 100 mM ammonium bicarbonate buffer, pH 8.4, and exactly 250 μg of oxidized insulin B-chain was added. The final volume was 500 μl. Samples were incubated for 3.5 hr at 37° C. 20 μl aliquots (corresponding to an initial insulin concentration of 10 μg) were boiled in loading buffer to stop the reaction and loaded onto a 22% polyacrylamide gel. 10 μg of purified insulin was used as a control.

General Methods

SDS-PAGE was performed according to Laemmli (22) in 22% gels. Protein concentrations were determined with the BioRad protein assay using bovine serum albumin as a standard.

EXAMPLE 1

Construction of ompT degp Mutants

Two mutations were combined in a single strain using P1 transduction to transfer chromosomal DNA from ompT mutant, *Escherichia coli* strain UT4400, into a degP mutant strain KS474. Strain UT4400 is a spontaneous mutant in which the entire ompT gene together with a sizable piece of adjacent DNA has been deleted from the chromosome. Strain KS474 contains a gene that confers resistance to the antibiotic kanamycin at the position where the degP gene is normally located. Cells were selected for resistance to kanamycin and to colicin D (resistance to this compound is encoded by one of the genes deleted from ompT mutant strain UT4400). In addition, the absence of OmpT was tested by examining the outer membrane proteins by electrophoresis (16)

EXAMPLE 2

Construction of ptr Mutants

Figure 1:
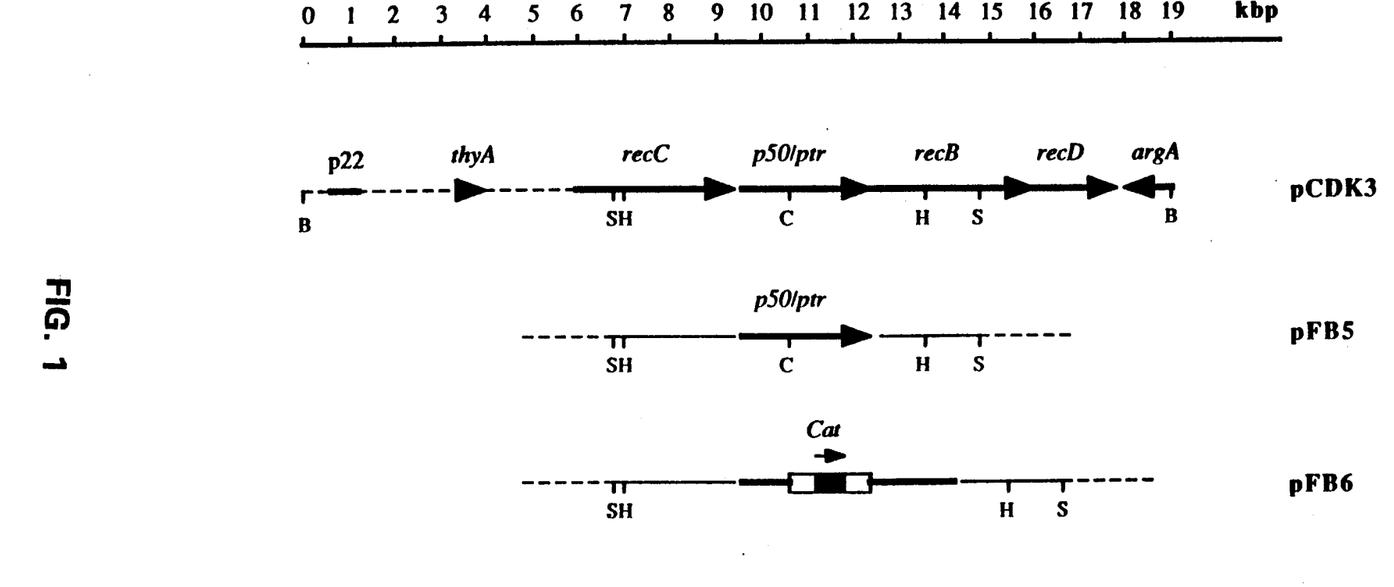
FIG. 1 shows the construction of the dtr32::Cat$^r$ mutation. Only the relevant portions of the plasmid are shown. Restriction site abbreviations are: B, BamH I; Ca, ClaI; H, Hind III; and S, Sal I.

The overall strategy used to construct ptr mutants is shown in FIG. 1. Plasmid pCDK3 which carries a 19 kbp insert mapping the thyA-argA region of the *E. coli* genome was digested with Sal I and BamH I. The 8 kbp Sal I fragment containing the ptr gene, was isolated by low melting point agarose. This DNA fragment was ligated into the unique Sal I site of plasmid pCS1 to yield plasmid pFB5. Plasmid pCS1 was itself generated by transferring the protein A-β-lactamase gene into a plasmid vector having a different origin of replication (16). pFB5 contains a unique Cla I site, located approximately 1000 bp downstream from the start codon of the ptr gene. A functional chloramphenicol acetyl transferase (Cat) gene was obtained in a 1.7 kbp Hinc II-Xmn I fragment from plasmid PACYC184. Plasmid pFB5 was linearized with Cla I, treated with Klenow to generate blunt ends, and ligated to the 1.7 kbp DNA fragment from pACYC184. Competent cells were transformed with the ligation mixture. Transformants were selected on chloramphenicol plates and tested for ampicillin resistance. The structure of the resulting plasmid, pFB6, was confirmed by restriction analysis.

Plasmid pFB6 was digested with Sal I and the 9.7 kbp fragment was isolated. The chloramphenicol resistance insertional mutation in the ptr gene was transferred to the *E. coli* chromosome. *E. coli* strain D301 carries a tetracycline resistance insertional mutation in the recD gene that allows the cells to be transformed with linearized DNA (23). Competent D301 cells were transformed with about 1.5 μg of the 9.7 kbp linearized DNA and plated on chloramphenicol plates. To ensure that no intact pFB6 had been cotransformed, the transformants were tested for ampicillin sensitivity. A chloramphenicol resistant (Cat$^r$), tetracycline resistant (Tet$^r$), ampicillin sensitive (Amp$^s$) colony, SF101, was selected. The ptr mutation was designated ptr32:::ΩCat$^r$. Since SF101 is a D301 derivative, it also contains the tetracycline resistance insertional mutation in its recD gene. The ptr mutation was transferred into bacterial strain KS272 by generalized P1 transduction. Transductants containing the ptr32:::ΩCat$^r$ mutation were isolated on the basis of chloramphenicol resistance. These colonies were further selected for tetracycline sensitivity to ensure that they did not contain the recD mutation present in D301. This process yielded an *E. coli* strain carrying a chloramphenicol resistance insertional mutation in the ptr gene as well as a functional recD gene, i.e. having an intact exonuclease V activity. The selected strain SF103 has been deposited with ATCC, Accession number 55100.

Figure 2:
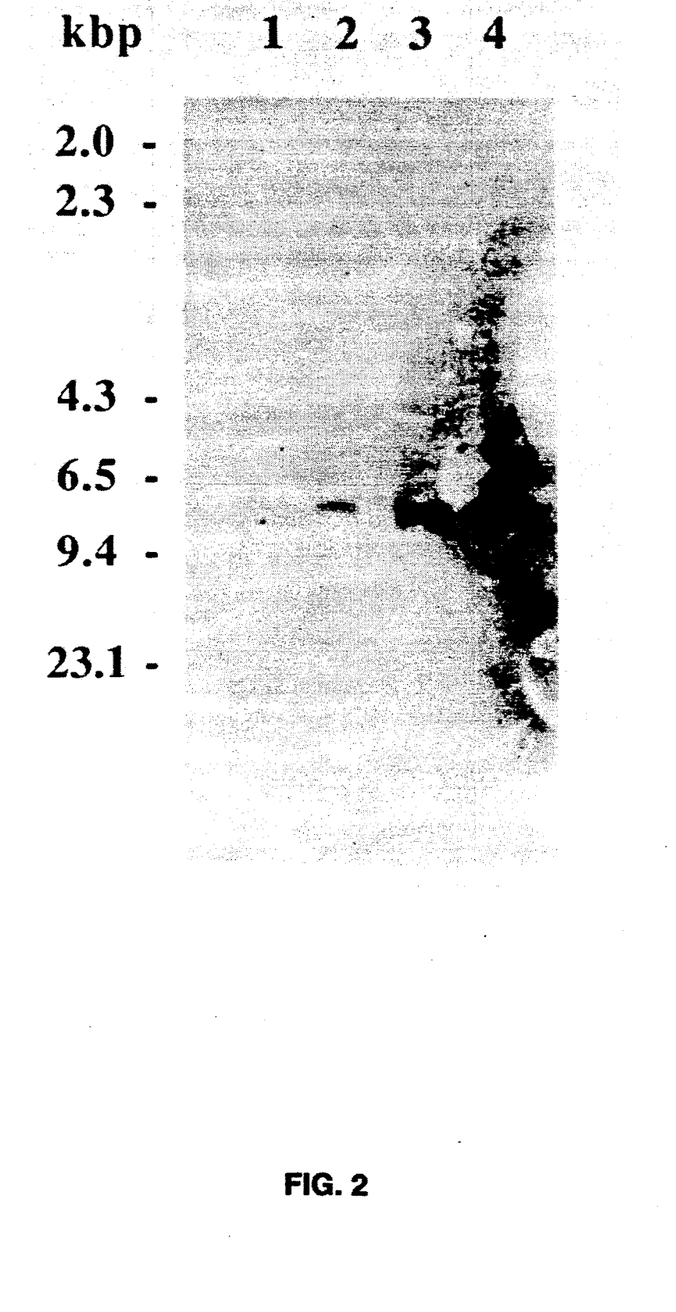
FIG. 2 is a Southern blot analysis of genomic DNA digested with Hind II and Cla I. Lane 1, KS272 (wild type); lane 2, SF 103 (ptr); lane 3, SF115 (ptr degP); lane 4, SF120 (ptr degP ompT).

The correct insertion of the chloramphenicol cartridge was confirmed by Southern blotting (FIG. 2). A Hinc II-Xmn I chloramphenicol probe derived from plasmid pACYC184 and labeled with digoxigenin-11-dUTP hybridized with Hinc II+Cla I digested genomic DNA from SF103 (lane 2) but did not hybridize with DNA from the parental strain KS272.

Figure 3:
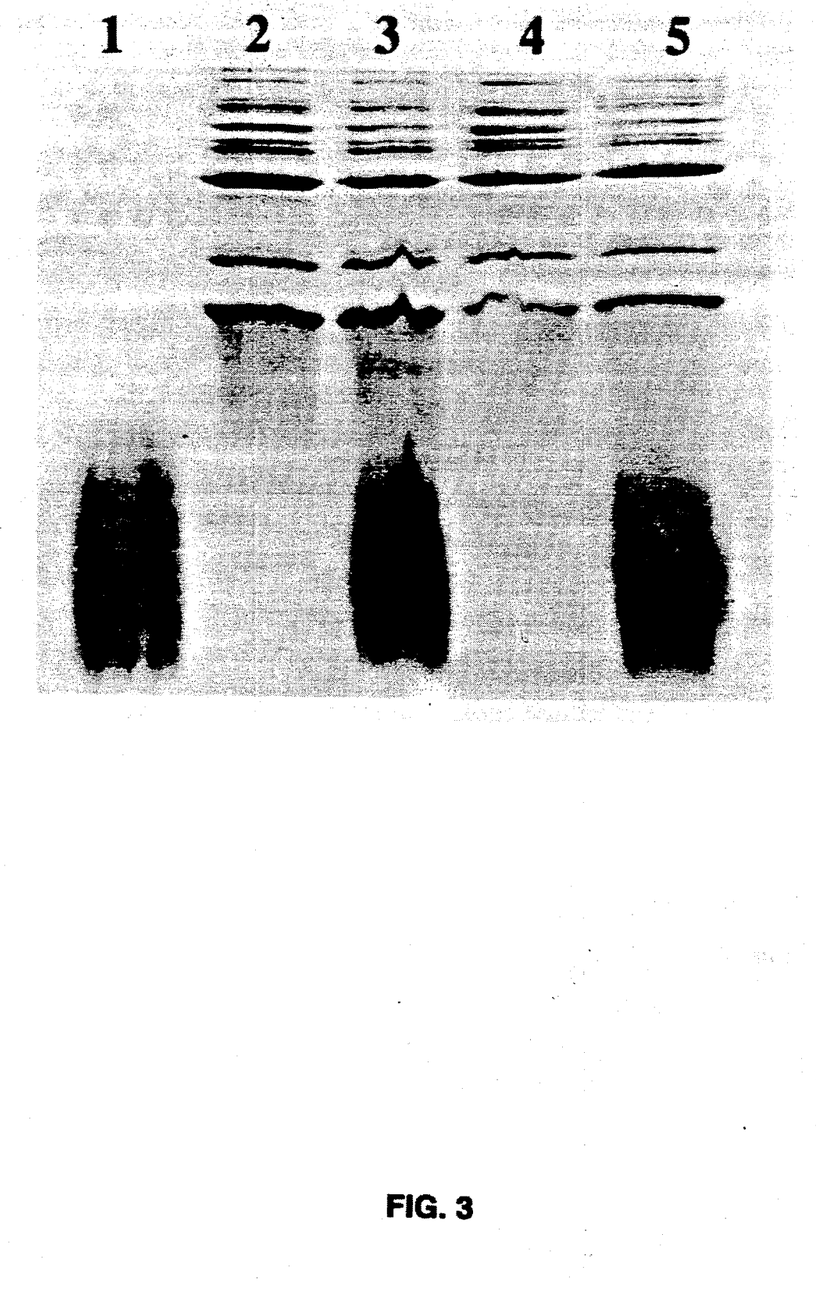
FIG. 3 shows the results of the insulin degradation assays. Lane 1, purified insulin control; lane 2, KS272 (wild type); lane 3, SF103 (ptr), lane 4, SF110 (ompT degP); lane 5, SF120 (ptr degP ompT).

Because Protease III is the only cell envelope protease which has been reported to rapidly degrade insulin, the absence of Protease III proteolytic activity in the ptr32:::ΩCat$^r$ mutant SF103 was demonstrated as follows. Strains KS272 and SF103 were grown in LB medium supplemented with glucose and the appropriate antibiotics for 24 hours. The periplasmic fraction of the cells was collected by the method of Nossal and Heppel (21) and concentrated by ultrafiltration. Periplasmic proteins were incubated with oxidized insulin B-chain and resolved by SDS-PAGE as described in Materials and Methods. FIG. 3 shows that no appreciable degradation was observed with SF103 (lane 3). In contrast, no intact insulin could be detected after incubation with the osmotic shock fractions of the isogenic strains KS272 (lane 2). Therefore, the ptr32::ΩCat$^r$ mutant SF103 does not possess the insulin degrading activity typical of strains containing an intact Protease III activity.

Finally, the presence of an intact exonuclease V activity in SF103 was demonstrated in the following manner. *E. coli* cells containing a defective exonuclease V enzyme (e.g., a mutation in one or more of the recB, recC and recD genes) are fully permissive for bacteriophage T4 gene 2 mutants (T4 2−). However, T4 2− is unable to infect cells containing an intact exonuclease V activity. Strains JC7729, KS272 and SF103 were infected at different multiplicities of infection with T4 2−(amN51) as described (24). Although T4 2− formed numerous plaques on the recB strain JC7729 (the titer of the phage was about $3 \times 10^9$ PFU/ml on JC7729), none were obtained on KS272 or SF103, indicating the presence of a fully functional exonuclease V in these strains. Furthermore, streaks of SF103 cells exposed to 1.1 mW of UV radiation per cm$^2$ for up to 100 seconds did not display the reduced viability typically observed in recB recC recD mutants. The ptr mutant SF103 grew to an optical density at 600 nm of about 1.8 in a variety of media (e.g., LB, M9, W salts).

EXAMPLE 3

Construction of ptr degP Mutants

P1 generalized transduction was used to transfer the ptr32::ΩCat$^r$ mutation from SF101 to a degP mutant KS474. Transductants were selected for chloramphenicol resistance and tetracycline sensitivity to confirm the presence of the ptr mutation and the absence of the recD mutation respectively. The resulting colonies were further tested for kanamycin resistance, indicating the presence of the degP mutation.

The resulting double protease-deficient strain, SF115, was tested for (i) proper insertion of the chloramphenicol resistance cartridge (FIG. 2, lane 3), (ii) absence of proteolytic activity against insulin, and (iii) presence of an intact exonuclease V activity, with a series of tests as described in Example 2.

EXAMPLE 4

Construction of ptr ompT Mutants

Mutants in both ptr and ompT were constructed in a manner analogous to that used for the construction of the ptr degP double mutant SF115, described in Example 3, except that P1 generalized transduction was used to transfer the ptr32::ΩCat$^r$ mutation from SF101 to SF100. The latter strain contains a deletion in the chromosome which includes the ompT gene (16). Transductants were selected for chloramphenicol resistance and tetracycline sensitivity to confirm the presence of the ptr mutation and the absence of the recD mutation, respectively.

The resulting double protease-deficient strain SF112, was tested for (i) proper insertion of the chloramphenicol resistance cartridge, (ii) absence of proteolytic activity against insulin, and (iii) presence of an intact exonuclease V activity, as described in Example 2.

EXAMPLE 5

Construction of ptr degP ompT Mutants

Generalized P1 transduction was used to transfer the ptr32::ΩCat$^r$ mutation from strain SF101 obtained as described in Example 2 into ompT degP mutants as obtained in Example 1. Transductants were selected for chloramphenicol resistance and tetracycline sensitivity to confirm the presence of the ptr mutation and the absence of the recD mutation, respectively. The resulting colonies were further tested for kanamycin resistance, indicating the presence of the degP mutation. The selected triply protease-deficient mutant strain was designated SF120 and is on deposit with ATCC, Accession number 55099.

Strain SF120 was tested for (i) proper insertion of the chloramphenicol resistance cartridge (FIG. 2, lane 4), (ii) absence of proteolytic activity against insulin (FIG. 3, lane 5), and (iii) presence of an intact exonuclease V activity, with a series of tests as described in Example 2.

EXAMPLE 6

Expression of Protein A-β-Lactamase from Protease-Deficient Mutants

Figure 4:
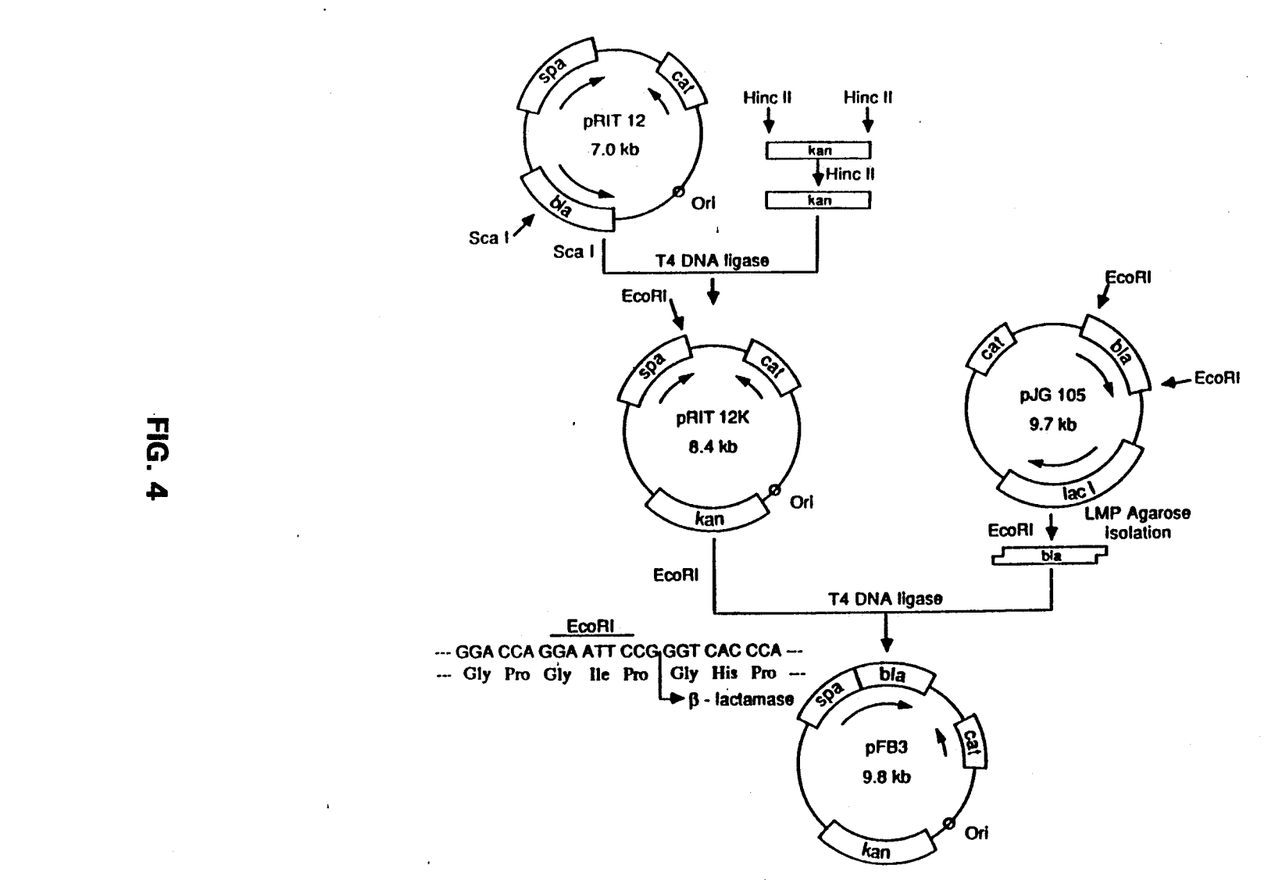
FIG. 4 shows the construction of plasmid vector pBF3, indicating restriction sites, localization of origins of replication, and the nucleotide sequence at the junction of protein A and mature β-lactamase gene. Boxes show the relative position of genes coding for β-lactamase (bla), protein A (spa), chloramphenicol acetyl transferase (cat), tetracycline resistance (tet) and lac I.

Plasmid pFB3 encodes a hybrid protein constructed by in-frame fusion of the genes coding for Staphylococcus aureus protein A and the *E. coli* enzyme TEM β-lactamase (FIG. 4). β-lactamase is a small, monomeric enzyme involved in the hydrolysis of the β-lactam ring of many antibiotics such as penicillin, nitrocefin, and cephaloridine. β-lactamase activity against the substrate benzylpenicillin was determined using the spectrophotometric methods described in Materials and Methods.

The protease-deficient mutants described in Examples 1 to 6 were shown to augment the expression of protein A-β-lactamase as follows: Strains KS272, KS474, SF103, SF110, SF115 and SF120 were transformed with the plasmid vector pFB3. Cultures were grown for 24 hours in LB medium and the total penicillinase activity was assayed as described in Materials and Methods. Penicillinase specific activities of these strains are shown in Table II.

TABLE II

Influence of different protease-deficient mutant strains on the expression of protein A-β-lactamase from the plasmid vector pFB3.

| Strain (plasmid) | Strain Characteristics | | | Growth medium | Total penicillinase specific activity (U/mg) ± SD | % increase |
| --- | --- | --- | --- | --- | --- | --- |
| KS272(pFB3) | ompt+ | degP+ | ptr+ | LB | 15.2 + 2.9 | — |
| KS474(pFB3) | ompT+ | degP | ptr+ | LB | 47.9 ± 8.3 | 215 |
| SF100(pFB3) | ompT | degP+ | ptr+ | LB | 28.2 ± 7.1 | 85 |
| SF103(pFB3) | ompT+ | degP+ | ptr | LB | 32.6 ± 12.5 | 115 |
| SF110(pFB3) | ompT | degP | ptr+ | LB | 87.9 ± 17.2 | 478 |
| SF115(pFB3) | ompT+ | degP | ptr | LB | 77.5 ± 16.5 | 410 |

TABLE II-continued

Influence of different protease-deficient mutant strains on the expression of protein A-β-lactamase from the plasmid vector pFB3.

| Strain (plasmid) | Strain Characteristics | | | Growth medium | Total penicillinase specific activity (U/mg) ± SD | % increase |
|---|---|---|---|---|---|---|
| SF120(pFB3) | ompT | degP | ptr | LB | 86.9 ± 10.1 | 427 |

Table II indicates that a single mutation in the ptr gene (strain SF103 described in Example 2) increased the expression of protein A-β-lactamase by about 2-fold compared to the parental strain KS272. This improvement is comparable to that observed with the single ompT mutant SF100 (lane 3). An approximate 3-fold increase in expression is obtained with the single degP mutant KS474. Use of the double mutants SF110 (ompT degP) and SF115 (ptr degP) described in Examples 1 and 3, respectively, increases the expression of protein A-β-lactamase by more than 5-fold relative to the parental strain KS272. The triple mutant SF120 (ptr degP ompT) described in Example 5, also provided a 5 to 6-fold increase in protein A-β-lactamase expression.

Figure 5:
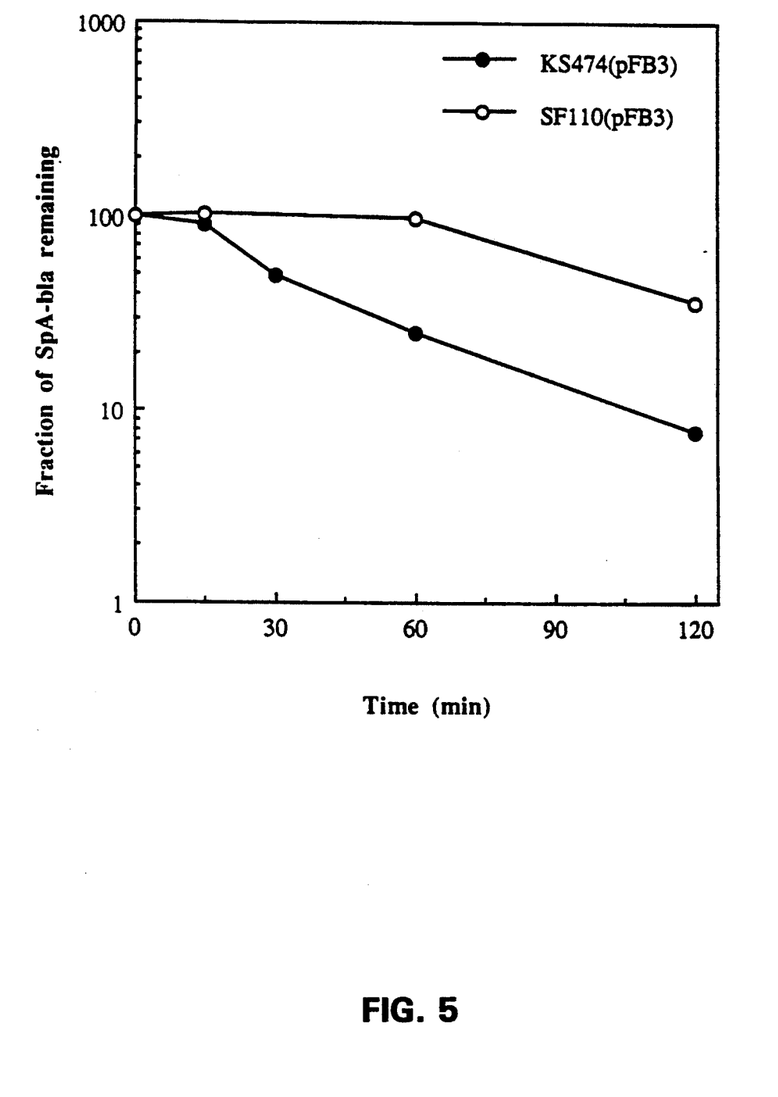
FIG. 5 shows the results of a pulse chase analysis of the stability of protein A-β-lactamase in the degP strain KS474 (solid circles) and the ompT degP mutant SF110 (open circles). The fraction of protein A-β-lactamase (SpA-bla) remaining corresponds to the intensity of the band at the specified time divided by the intensity at time zero, as determined by scanning of the X-ray film.

Enhanced expression levels of protein A-β-lactamase in the ompT degP double mutant SF110 were confirmed by radioactive pulse-chase experiments as described in Materials and Methods. FIG. 5 shows that the half-life of the fusion protein was approximately 30 min in the degP single mutant strain KS474, but was increased to about 100 minutes in the ompT degP double mutant strain SF110. Essentially no degradation of the fusion protein was evident in the double mutant for the first hour following the initiation of the chase, demonstrating that E. coli strains deficient in multiple proteases also provide enhanced levels of expression of protein A-β-lactamase in exponentially growing cells.

Figure 6:
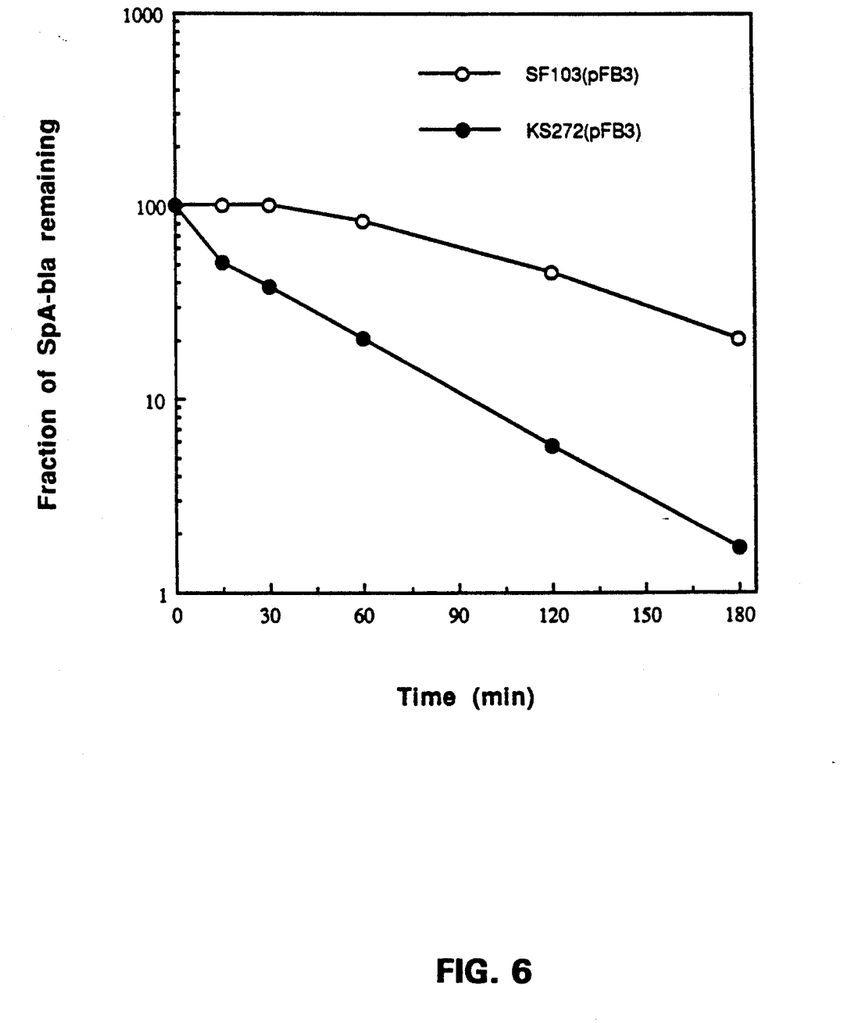
FIG. 6 shows the result of an analysis of the stability of protein A-β-lactamase in the wild type strain KS272 (solid circles) and the ptr mutant SF103 (open circles). The fraction of protein A-β-lactamase remaining was determined as in FIG. 5.

Similarly, no degradation of protein A-β-lactamase was observed in the ptr mutant SF103 for the first 30 minutes following the initiation of the chase (FIG. 6).

EXAMPLE 7

Effect of Medium, pH and Metal Ions on Protein A-β-Lactamase Expression in Protease-Deficient Mutants Strains SF110 (ompT degP) and SF120 (ptr degP ompT) were transformed with plasmid vector pFB3 and grown in M9 medium. Total specific penicillinase activities were measured. The introduction of a ptr mutation in the degP, ompT background resulted in a reproducible 33% increase in protein A-β-lactamase expression, as shown in Table III.

TABLE III

Total penicillinase activities of double and triple protease-deficient mutants transformed with the plasmid vector pFB3.

| Strain (plasmid) | Strain Characteristics | | | Growth medium | Total penicillinase specific activity (U/mg) ± SD | % increase |
|---|---|---|---|---|---|---|
| SF110(pFB3) | ompT | degP | ptr+ | M9 | 4.8 ± 0.4 | — |
| SF120(pFB3) | ompT | degP | ptr | M9 | 6.4 ± 0.8 | 33 |

The effect of zinc chloride addition to protease-deficient cells grown in minimal medium W salts is shown in Table IV. Protein A-β-lactamase expression from SF110 harboring plasmid vector pFB3 was increased by 46% when 0.1 mM ZnCl$_2$ was added to the medium. The effect on SF120 cells harboring pFB3 was an increase of 53% when grown under the same conditions.

TABLE IV

Effect of zinc chloride addition to the growth medium of cells deficient in multiple proteases on the expression of protein A-β-lactamase from the plasmid vector pFB3.

| Strain (plasmid) | Strain characteristics | | | Growth medium | Relative penicillinase specific activity (% ± SD) |
|---|---|---|---|---|---|
| SF110(pFB3) | ompT | degP | ptr+ | W | 100 |
| SF110(pFB3) | ompT | degP | ptr+ | W + 0.1 mM ZnCl$_2$ | 146 ± 6 |
| SF120(pFB3) | ompT | degP | ptr | W | 100 |
| SF120(pFB3) | ompT | degP | ptr | W + 0.1 mM ZnCl$_2$ | 153 ± 9 |

Figure 7:
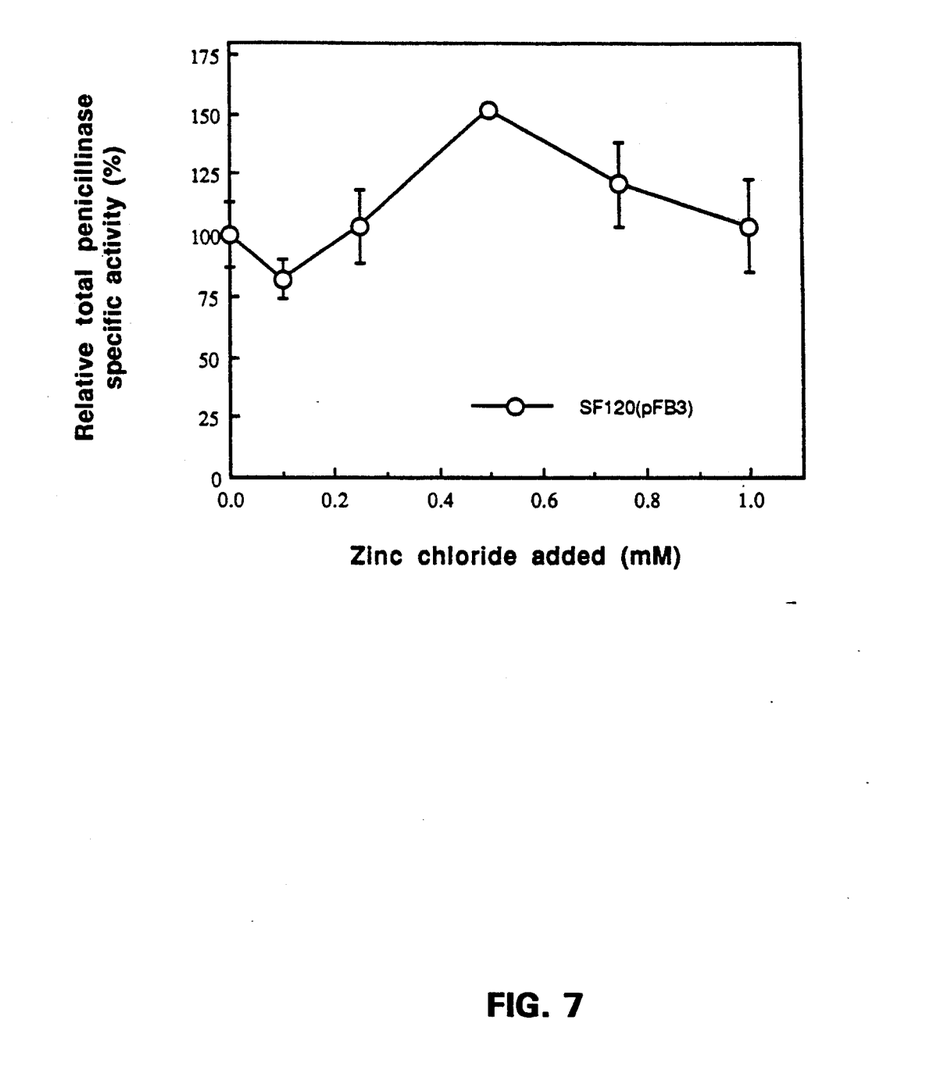
FIG. 7 shows the effect of zinc chloride addition on the expression of protein A-β-lactamase from the ptr degP ompT mutant SF120. Relative activities represent the ratio of the total penicillinase specific activity of cultures containing a given concentration of zinc chloride to the total penicillinase specific activity of cultures without zinc chloride.

Triply protease-deficient SF120 cells transformed with the plasmid expression vector pFB3 were grown in complex medium LB to which up to 1 mM zinc chloride was added. As shown in FIG. 7, maximum expression of protein A-β-lactamase was observed when approximately 0.5 mM Zn$^{+2}$ was added to the medium.

Figure 8:
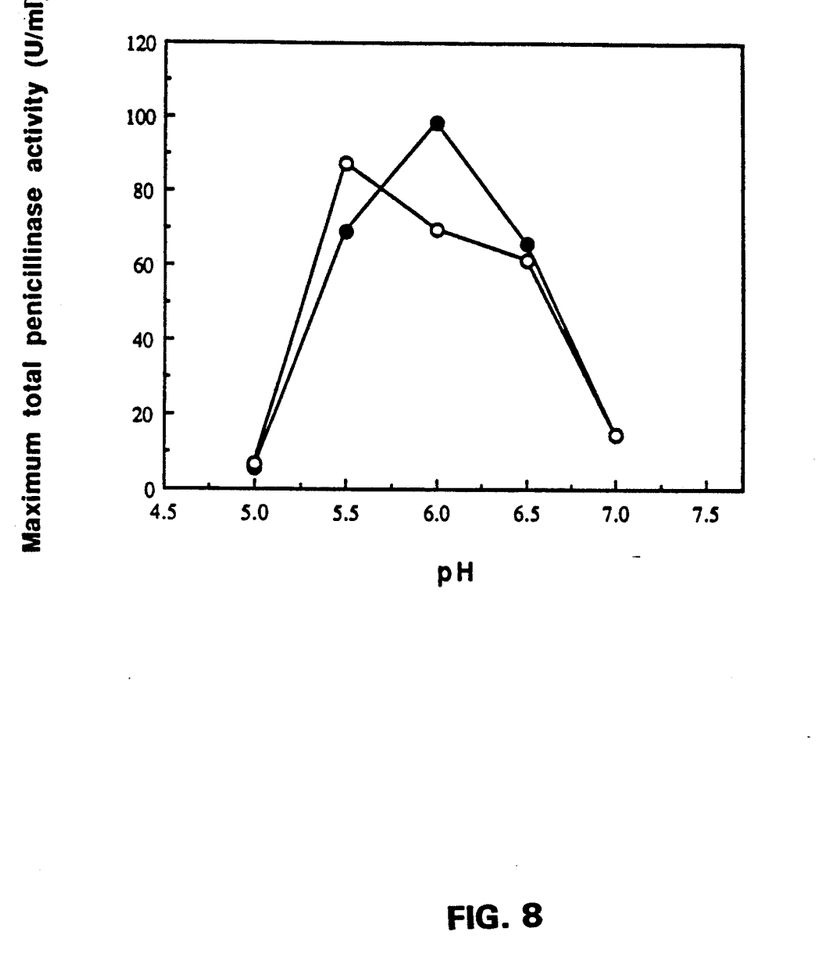
FIG. 8 shows the effect of pH on the expression of protein A-β-lactamase. Maximum total penicillinase activities of KS474 (degP) (solid circles) and SF110 (ompT degP) (open circles) cells harboring the plasmid vector pFB3 are plotted versus pH.

The effect of pH on protein A-β-lactamase expression in cells transformed with plasmid vector pBF3 was determined. Fermentations were carried out in Bioflo III fermenters with a working volume of 2 liters and followed for 24 hrs. The pH was maintained at a constant value by automatic addition of 1 M HCl or 1 M NaOH to growth medium LB supplemented with 0.2% glucose and 50 μg/ml ampicillin. Fermenters were inoculated with 25 or 50 ml of transformed E. coli strain KS474, deficient in degP, or SF110, deficient in ompT and degP. FIG. 8 shows that maximum expression of the fusion protein was obtained when the pH was maintained between 5.5 and 6.0.

PROPHETIC EXAMPLE 8

The present example outlines the procedure contemplated by the Applicants to be useful for the successful preparation of a mutant bacterium deficient in four proteases.

Construction of ptr ompT degP Protease VI Mutants

Construction of mutant organisms will involve the following steps: (1) cloning and amplification of a gene or part of a gene of a protease; (2) mutagenesis of the isolated gene sequence to allow easy selection of the mutants; (3) recombination of the mutated gene sequence into the chromosome; and (4) transfer of the mutation into a strain deficient in three proteases.

Protease VI is isolated and purified from *Escherichia coli* using well known techniques (25-27). The amino terminal sequence of the purified protein is determined by gas phase sequencing. Degenerate oligonucleotide primers corresponding to the sequence of the first six or seven N-terminal amino acids are prepared by automated solid phase synthesis (19). The primers are designed so that a suitable restriction site is generated upon annealing to a plasmid library of *E. coli* genomic DNA. Amplification is carried out by polymerase chain reaction (PCR) using an additional primer which corresponds to a plasmid sequence The amplified DNA is isolated and subcloned within a suitable vector containing appropriate restriction sites. The gene or part of the gene thus amplified is then used to screen an ordered plasmid *E. coli* library so that the gene is identified in the physical map of the genome, subsequently allowing the entire gene to be cloned. Once the protease gene has been cloned on a plasmid, mutations are generated either in vitro as described in Example 2 or in vivo by employing transposon mutagenesis with Tn10 which is a transposon carrying tetracycline resistance. A mutation resulting in deletion of a substantial fraction of the gene's DNA and linked to the antibiotic resistance gene is then isolated. The mutation is then transferred into the triple mutant strain SF120 to generate a quadruple mutant strain exhibiting substantial reduction in four protease activities. Strains in which the transposon has been excised are isolated by screening for cells that have lost the selectable marker. These cells will not exhibit tetracycline resistance but will be defective in Protease VI as well as OmpT, DegP and Protease III.

REFERENCES

The references listed below are incorporated herein by reference to the extent they supplement, explain, provide a background for or teach methodology, techniques and/or compositions employed therein.

1. Georgiou, G., AIChE. J. 34, 1233-1248 (1988).
2. Huse, W. D., Lakshmi, S., Iverson, S. A., Kang, A. S., Alting-Mees, M., Burton, D. R., Benkovic, S. J. and Lerner, R. A., Science 246, 1275-1280 (1989).
3. Baneyx, F. and Georgiou, G., in Stability of Protein Pharmaceuticals: Chemical and Physical Pathways of Protein Degradation in press.
4. Goldberg, A. L. and St. John, A. C., Ann. Rev. Biochem. 45, 747-803 (1976).
5. Hershko, A. and Ciechanover, A., Ann. Rev. Biochem. 51, 335-364 (1982).
6. Lazdunski, A. M., FEMS Microbiol. Rev. 63, 265-276 (1989).
7. Miller, C. G. in *Escherichia coli* and *Salmonella typhimurium:* Cellular and Molecular Biology, Vol. 1, F. C. Neidhardt, Ed., American Society for Microbiology, Washington, DC, pp 680-691, 1987.
8. Field, H., Rees, A. R., Yarranton, G. T., WO 89/02465, Mar. 23, 1989.
9. Beckwith, J. R. and Strauch, K. L., WO 88/05821, Aug. 11, 1988.
10. Chaudhury, A. and Smith G. R., J. Bacteriol. 160, 788-791 (1984).
11. Elish, M. E., Pierce, J. R. and Earhart, C. F., J. Gen. Microbiol. 134, 1355-1364 (1988).
12. McIntosh, M. A., Chenault, S. S. and Earhart, C. F., J. Bacteriol. 137, 653-657 (1979).
13. Cheng, Y. S. E. and Zipser, D., J. Biol. Chem. 254, 4698-4706 (1979).
14. Strauch, K. and Beckwith, J. Proc. Natl. Acad. Sci. U.S.A. 85, 1576-1580 (1988).
15. Baneyx, F. and Georgiou, G., Enzyme Microb. Technol. 11, 559-567 (1989).
16. Baneyx, F. and Georgiou, G., J. Bacteriol. 172, 491-494 (1990).
17. Smith, G. R., Halpern, Y. S. and Magasanik, J. Biol. Chem. 246, 3320-3329 (1971).
18. Maniatis, T., Fritsch, E. F. and Sambrook, J. in Molecular Cloning: A Laboratory Manual, Cold Spring Harbor, NY, Cold Spring Harbor Laboratory Press, 1982.
19. Ausubel, F. M., Brent, R., Kingston, R. E., Moore, D. D., Seidman, J. G., Smith, J. A. and Struhl, K. in Current Protocols in Molecular Biology, John Wiley & Sons, New York, NY (1987).
20. Georgiou, G., Shuler, M. L. and Wilson, D. B., Biotechnol. Bioeng. 32, 741-748 (1988).
21. Nossal, N. G. and Heppel, L. A., J. Biol. Chem. 241, 3055-3062 (1966).
22. Laemmli, U. K., Nature (London) 227, 680-685 (1970).
23. Russell, C. B., Thaler, D. S. and Dahlquist, F. W., J. Bacteriol. 171, 2609-2613 (1989).
24. Weichenhan, D. and Wachkernagel, W., Molecular Microbiology 3, 1777-1784 (1989).
25. Swamy, S. K. H. and Goldberg, A. L., J. Bacteriol. 149, 1027-1033 (1982).
26. Palmer, S. M. and St. John, A. C., J. Bacteriol. 169, 1474-1479 (1987).
27. PaCaud, M., J. Biol. Chem. 257, 4333-4339 (1982).
28. Strauch, K. L., Johnson, K. and Beckwith, J., J. Bacteriol. 171, 2689-2696 (1989).
29. Chang, A. C. Y. and Cohen, S. N., J. Bacteriol. 134, 1141-1156 (1978).
30. Dykstra, C. C., Prasher, D. and Kushner, S. R., J. Bacteriol. 157, 21-27 (1984).

What is claimed is:

1. A genetically engineered *Escherichia coli* or *Salmonella typhimurium* bacterium deficient in chromosomal genes ptr, ompT and degP encoding proteases Protease III, OmpT, and DegP, respectively.

2. A genetically engineered *Escherichia coli* or *Salmonella typhimurium* bacterium deficient in chromosomal genes degP and ompT encoding DegP and OmpT, respectively.

3. A genetically engineered *Escherichia coli* or *Salmonella typhimurium* bacterium deficient in chromosomal genes degP and ptr encoding proteases DegP and Protease III respectively.

4. A genetically engineered *Escherichia coli* or *Salmonella typhimurium* bacterium deficient in chromosomal genes ompT and ptr encoding proteases OmpT and Protease III respectively.

5. A mutant *E. coli* strain SF 120 having ATCC accession number 55099 deposited Oct. 10, 1990.

6. A mutant *E. coli* strain SF 110 having ATCC accession number 55101 deposited Oct. 10, 1990.

* * * * *